(12) United States Patent
Yamamoto

(10) Patent No.: US 8,776,856 B2
(45) Date of Patent: Jul. 15, 2014

(54) ULTRASONIC JOINING APPARATUS AND ABSORBENT ARTICLE MANUFACTURING APPARATUS

(75) Inventor: Hiroki Yamamoto, Kagawa (JP)

(73) Assignee: Uni-Charm Corporation, Ehime-ken (JP)

(*) Notice: Subject to any disclaimer, the term of this patent is extended or adjusted under 35 U.S.C. 154(b) by 351 days.

(21) Appl. No.: 13/383,636

(22) PCT Filed: Jul. 30, 2010

(86) PCT No.: PCT/JP2010/062937
§ 371 (c)(1),
(2), (4) Date: Jan. 31, 2012

(87) PCT Pub. No.: WO2011/013819
PCT Pub. Date: Feb. 3, 2011

(65) Prior Publication Data
US 2012/0175064 A1 Jul. 12, 2012

(30) Foreign Application Priority Data
Jul. 31, 2009 (JP) ................................ 2009-180199

(51) Int. Cl.
B32B 37/00 (2006.01)
B29C 65/08 (2006.01)

(52) U.S. Cl.
CPC ............... *B29C 65/086* (2013.01); *B29C 65/08* (2013.01)
USPC .................................... 156/580.2; 156/580.1

(58) Field of Classification Search
USPC ......... 156/73.1, 580.1, 580.2; 228/1.1, 110.1; 425/174.2; 264/442, 443, 444, 445
See application file for complete search history.

(56) References Cited

U.S. PATENT DOCUMENTS 5,733,411 A 3/1998 Bett
5,871,605 A 2/1999 Bett
(Continued)

FOREIGN PATENT DOCUMENTS

GB 2257652 A 1/1993
JP 61073502 S 5/1986
(Continued)

OTHER PUBLICATIONS

International Search Report and Written opinion for PCT/JP2010/062937 dated Aug. 31, 2010.
(Continued)

*Primary Examiner* — James Sells
(74) *Attorney, Agent, or Firm* — Lowe Hauptman & Ham LLP

(57) ABSTRACT

An anvil includes a base and projections and. The base is installed at an attachment position on an outer peripheral surface of a rotating drum. The projection protrudes from a front surface of the base in a normal direction H of the rotating drum and is formed in a line shape extending in the cross direction CD along the front surface of the base. On the front surface of the base, one end in the cross direction CD of the projection is provided forward of the other end in a rotation direction R. In the projection, a cut portion is formed to extend in a direction opposite to the protrusion direction of each protrusion. The cut portion extends from the front surface of the projection, protruding from the front surface of the base, to the vicinity of the middle of the projection.

7 Claims, 13 Drawing Sheets

(56) References Cited

U.S. PATENT DOCUMENTS

| | | | |
|---|---|---|---|
| 7,383,865 B2 | 6/2008 | Umebayashi et al. | |
| 7,887,652 B2 * | 2/2011 | Yamamoto | 156/64 |
| 7,887,656 B2 * | 2/2011 | Yamamoto | 156/73.1 |
| 8,074,693 B2 * | 12/2011 | Yamamoto et al. | 156/510 |
| 8,172,971 B2 * | 5/2012 | Yamamoto | 156/73.1 |
| 8,596,324 B2 * | 12/2013 | Yamamoto | 156/461 |
| 2004/0106506 A1 | 6/2004 | Ninomiya et al. | |
| 2005/0145317 A1 | 7/2005 | Yamamoto | |

FOREIGN PATENT DOCUMENTS

| | | | |
|---|---|---|---|
| JP | 5015551 A | 1/1993 | |
| JP | 6009927 A | 2/1994 | |
| JP | 6098941 A | 4/1994 | |
| JP | 2000502961 A | 3/2000 | |
| JP | 2002355270 A | 12/2002 | |
| JP | 2004298413 A | 10/2004 | |
| JP | 2008253633 A | 10/2008 | |
| WO | 2005105410 A1 | 11/2005 | |
| WO | 2008/126748 | 10/2008 | |

OTHER PUBLICATIONS

Office Action mailed Oct. 28, 2013, corresponds to Chinese patent application No. 201080033967.X.
Office Action issued Nov. 12, 2013, corresponds to Eurasian patent application No. 201200200.
Notification of Grounds for Rejection mailed Jun. 4, 2013 for counterpart Japanese application No. 2009-180199.
Official Action mailed on May 28, 2013 for counterpart EA application No. 201200200.

* cited by examiner

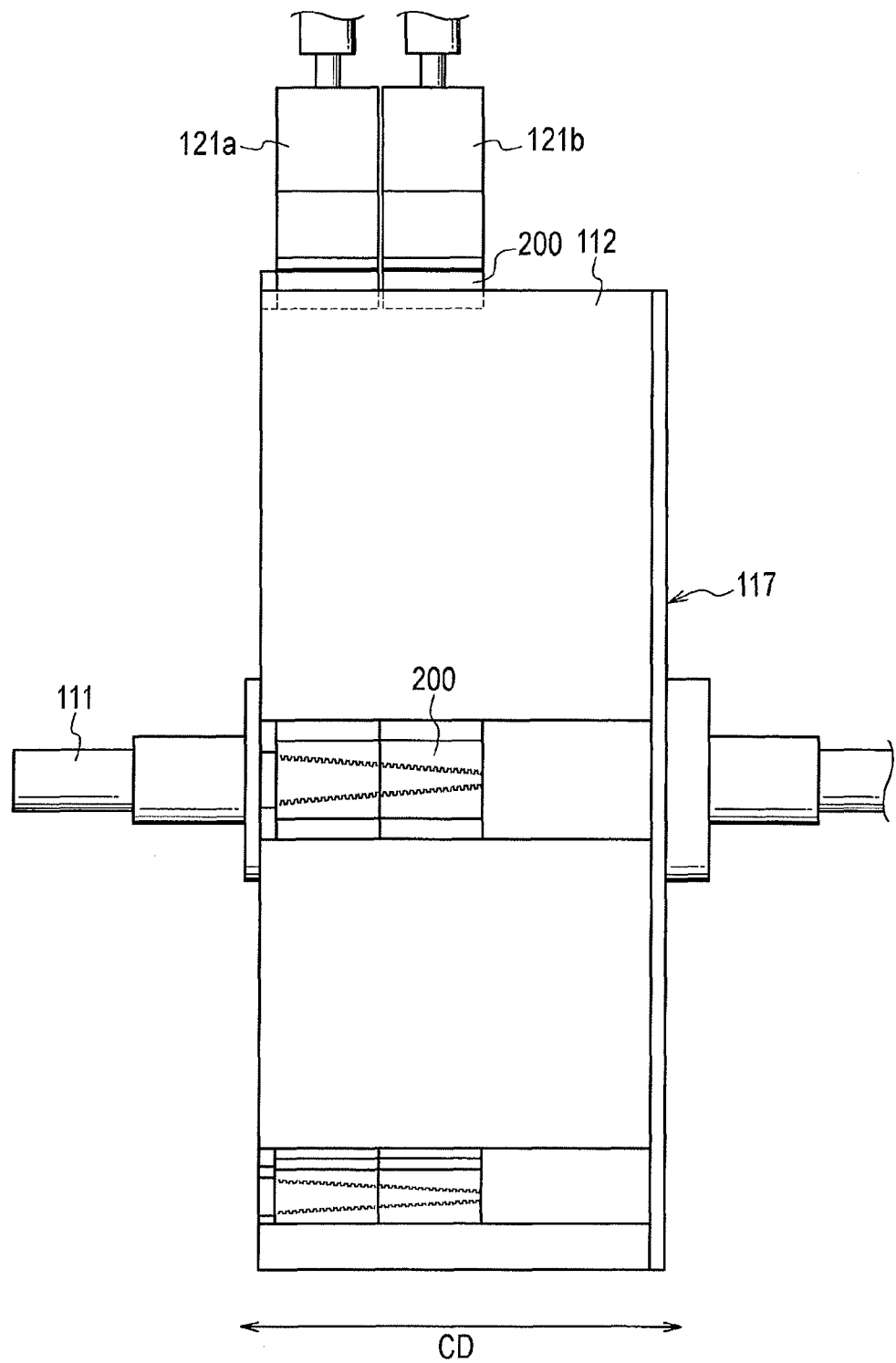

US 8,776,856 B2

ULTRASONIC JOINING APPARATUS AND ABSORBENT ARTICLE MANUFACTURING APPARATUS

RELATED APPLICATIONS

The present application is a National Phase of International Application Number PCT/JP 2010/062937, filed Jul. 30, 2010 and claims priority from Japanese Application Number 2009-180199, filed Jul. 31, 2009.

TECHNICAL FIELD

The present invention relates to an ultrasonic joining apparatus for joining a first web and a second web, and an absorbent article manufacturing apparatus for manufacturing a pants-type absorbent article by joining the first web to form a front waistline portion and the second web to form a back waistline portion.

BACKGROUND ART

An absorbent article such as a disposable diaper generally includes: a front waistline portion to be fitted to the front waist of a wearer; a back waistline portion to be fitted to the back waist of the wearer; a crotch portion to be fitted to the crotch of the wearer; and leg-surrounding opening portions which open at both sides of the crotch portion. The front waistline portion and the back waistline portion are joined to each other at waist lateral-side portions.

In the steps of manufacturing a disposable diaper, a web is folded into two at the crotch portion by overlapping its first web to form the front waistline portion and its second web to form the back waistline portion with each other, and the web thus folded is joined at the left and right waist lateral-side portions, thereby forming the web into pants-type diapers. Ultrasonic joining using an ultrasonic joining apparatus is employed for the joining of the web at the left and right waist lateral-side portions (for example, Patent Document 1).

The ultrasonic joining apparatus includes: a rotating drum having an anvil formed thereon, the anvil being configured to form a joint pattern by which the front waistline portion and the back waistline portion are joined at the left and right waist lateral-side portions; and an ultrasonic horn configured to generate ultrasonic waves. The ultrasonic joining apparatus joins the first and second webs of the web, which is folded into two at the crotch portion, by pressing the ultrasonic horn intermittently against certain positions of the left and right waist lateral-side portions of the first and second webs while conveying the first and second webs between the rotating drum and the ultrasonic horn in a direction in which manufacturing processes flow.

The anvil includes: a projection being provided on the outer peripheral surface of the rotating drum and protruding in a normal direction of the rotating drum; and multiple protrusions protruding from the projection in the normal direction. When the ultrasonic horn is pressed against the anvil with the web interposed therebetween, the web is melted by being heated from the inside thereof, and is pressed against the protrusions protruding from the projection. As a result, a convexo-concave joint pattern is formed on the web.

Demand for diapers for adults has been growing in recent years. A diaper for adults is larger in size, and thus its manufacturing line is larger than a diaper for children. For example, since a waist lateral-side portion of the diaper for adults is longer than that of the diaper for children, the size of the anvil needs to be accordingly increased in length in a cross direction in a manufacturing line.

Thus, the following problems occur in the conventional ultrasonic joining apparatus. The ultrasonic horn is pressed against the anvil with the web interposed therebetween. Hence, if the anvil is large in size, damages caused by the mutual interference of vibrations generated by the ultrasonic horn are likely to be locally accumulated in the anvil or accumulated in a peripheral member connected to the anvil. This shortens the time to replace the anvil or the peripheral member, and increases manufacturing costs. Moreover, the damages on the anvil result in a reduction in yield rate.

PRIOR ART DOCUMENT

[Patent Document]
[Patent Document 1] Japanese Patent Application Publication No. Hei. 5-15551 (pp. 2 and 3, FIG. 4)

SUMMARY OF INVENTION

An ultrasonic joining apparatus according to a first aspect includes: a rotating drum having an anvil formed on an outer peripheral surface of the rotating drum; and an ultrasonic horn configured to output ultrasonic vibrations. The rotating drum has a rotational shaft extending in parallel with a cross direction orthogonal to a machine direction in which manufacturing processes flow. The rotating drum and the ultrasonic horn are arranged to face each other with an intermediate web interposed therebetween, the intermediate web including a first web and a second web overlapping with each other. The anvil and the ultrasonic horn pinch a certain region of the intermediate web, which is conveyed in the machine direction, to perform ultrasonic joining on the certain region. The anvil includes: a projection protruding in a normal direction of the rotating drum and being formed in a line shape extending in the cross direction; and a plurality of protrusions protruding from the projection in the normal direction. The projection has a cut formed therein, the cut extending in a direction opposite to a protrusion direction of the protrusions.

BRIEF DESCRIPTION OF DRAWINGS

FIG. 13 is a side view showing the ultrasonic joining apparatus having modified ultrasonic horns seen from the downstream side.

DESCRIPTION OF EMBODIMENTS

Next, an embodiment of an ultrasonic joining apparatus and an absorbent article manufacturing apparatus according to the present invention is described with reference to the accompanying drawings. Note that, in the following description of the drawings, same or similar reference signs denote same or similar portions. In addition, it should be noted that the drawings are schematic and ratios of dimensions and the like are different from actual ones. Therefore, specific dimensions and the like should be determined in consideration of the following description. Moreover, the drawings also include portions having different dimensional relationships and ratios from each other.

(Structure of Absorbent Article)

Figure 1:
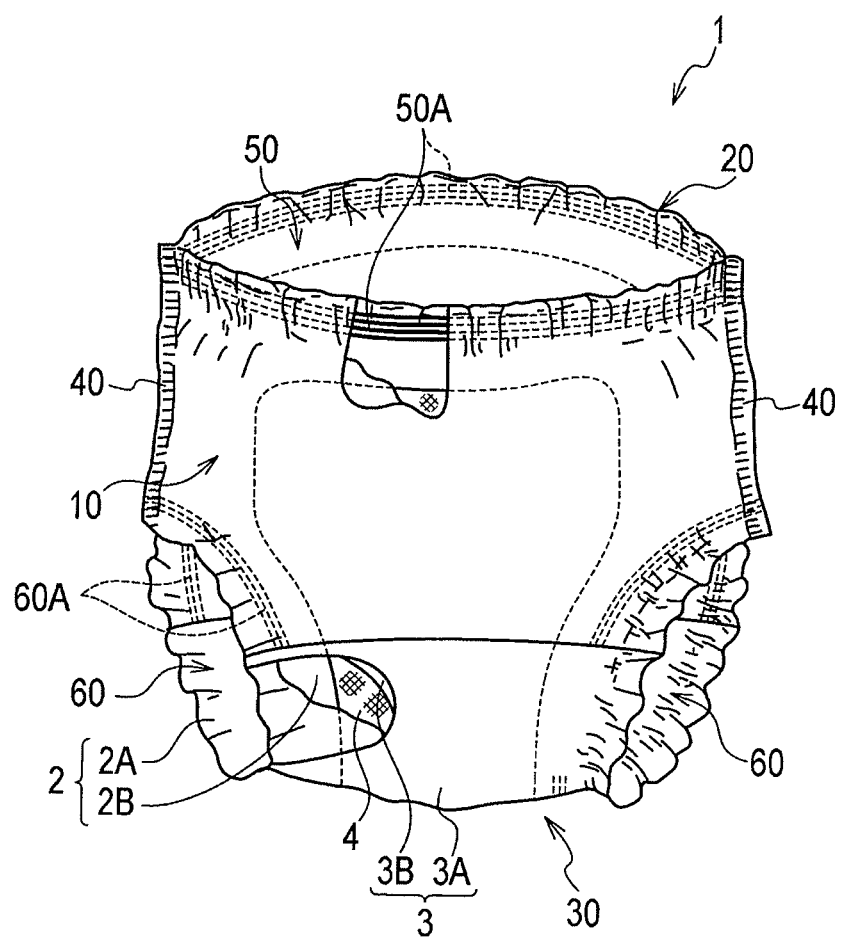
FIG. 1 is a perspective view showing an absorbent article according to an embodiment.

With reference to the drawing, description is first given of a structure of an absorbent article 1 manufactured by using an ultrasonic joining apparatus according to this embodiment. FIG. 1 is a perspective view showing the absorbent article 1 according to this embodiment.

In this embodiment, the absorbent article 1 is a disposable pants-type diaper. As shown in FIG. 1, the absorbent article 1 mainly includes a topsheet 2, a bottomsheet 3, and an absorber 4.

The topsheet 2 is provided at the innermost of the absorbent article 1 and to come into contact with the skin of a wearer. The topsheet 2 includes a top sheet 2A to come into contact with the wearer and a second sheet 2B joined to a surface, on the absorber 4 side, of the top sheet 2A. Note that, the topsheet 2 is made of a liquid permeable sheet such as a nonwoven fabric or perforated plastic film.

The backsheet 3 is provided at the outermost (on a side away from the wearer) of the absorbent article 1. The backsheet 3 includes a back sheet 3A provided at the outermost of the absorbent article 1 and a waterproof sheet 3B joined to a surface, on the absorber 4 side, of the back sheet 3A. Note that, the back sheet 3A is made of a nonwoven fabric or the like. The waterproof sheet 3B is made of a liquid impermeable sheet or the like.

The absorber 4 is provided between the topsheet 2 (the second sheet 2B) and the bottomsheet 3 (the waterproof sheet 3B), and absorbs bodily waste from the wearer.

The absorbent article 1 with the above structure is formed in combination of a front waistline portion 10 to be fitted to the front waist of the wearer, a back waistline portion 20 to be fitted to the back waist of the wearer, and a crotch portion 30 to be fitted to the crotch of the wearer (so-called three-piece type).

In the waist lateral-side portions of the wearer, the front waistline portion 10 and the back waistline portion 20 are joined at joint portions 40, and thereby form a waist opening portion 50 into which the body of the wearer is inserted. The crotch portion 30 is provided between the front waistline portion 10 and the back waistline portion 20. A waist gather 50A made of a stretchable rubber cord is provided to an entire peripheral edge of the waist opening portion 50. Leg-surrounding opening portions 60, into which the legs of the wearer are inserted, are formed on both sides of the crotch portion 30. A leg gather 60A made of a stretchable rubber cord is provided to an entire peripheral edge of each leg-surrounding opening portion 60.

(Method of Manufacturing Absorbent Article)

Figure 2:
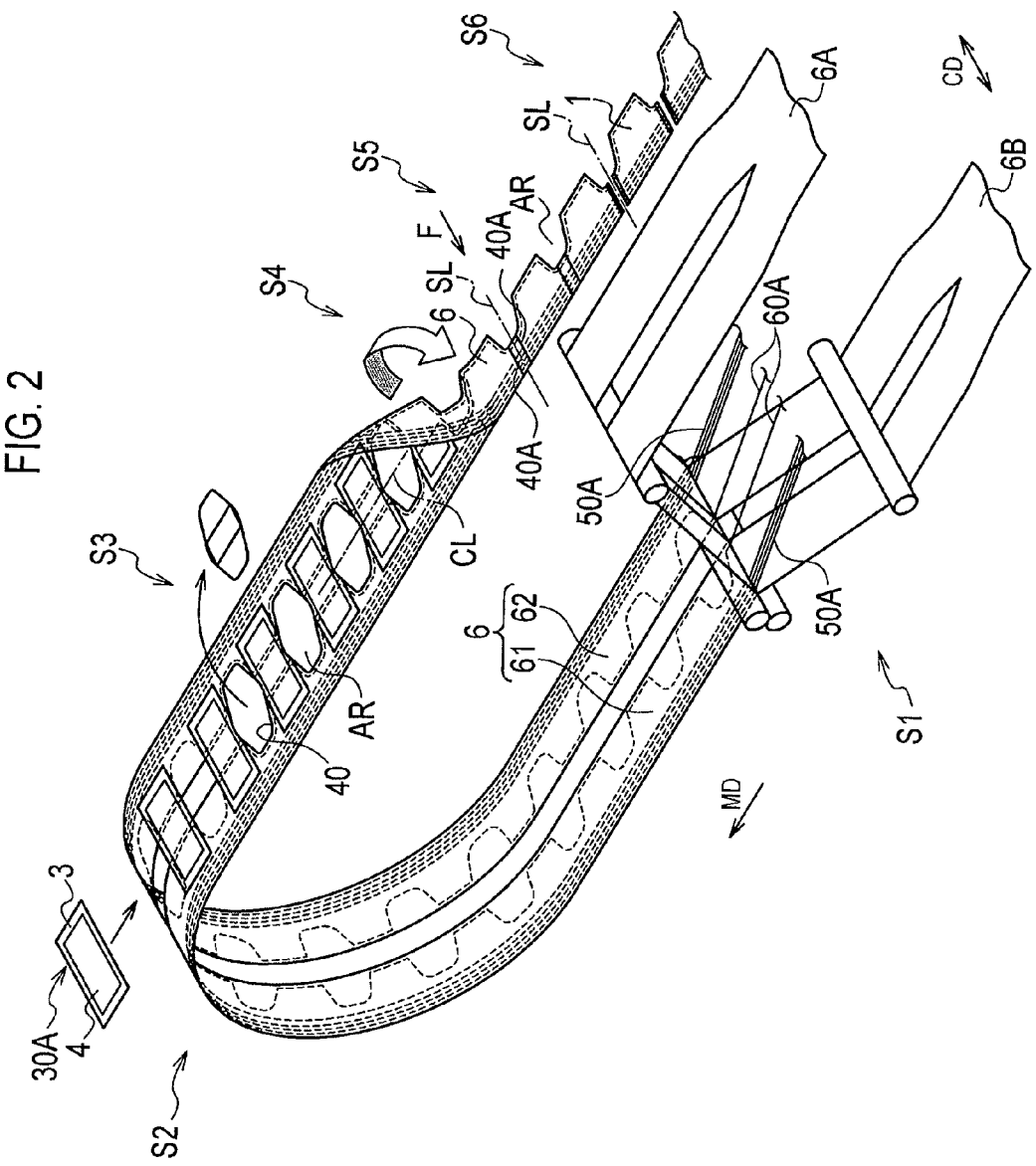
FIG. 2 is a diagram for explaining a part of a method of manufacturing the absorbent article according to this embodiment.

Next, a method of manufacturing an absorbent article according to this embodiment is described with reference to the drawing. FIG. 2 is a diagram for explaining a part of the method of manufacturing an absorbent article according to this embodiment.

As shown in FIG. 2, the method of manufacturing an absorbent article includes at least a waistline portion forming step S1, a crotch member transferring step S2, a leg-surrounding portion forming step S3, a folding step S4, a joining step S5, and a cutting step S6.

In the waistline portion forming step S1, gathers (the waist gather 50A and the leg gather 60A) are placed between a web 6A and a web 6B, and thereby a pair of webs 61 and 62 respectively prepared to form the front waistline portion 10 and the back waistline portion 20 are formed.

In the crotch member transferring step S2 after (downstream of) the waistline portion forming step Si, a crotch portion member 30A to form the crotch portion 30 is transferred (placed) between the pair of webs 61 and 62 at predetermined intervals in a machine direction MD.

In the leg-surrounding portion forming step S3 after (downstream of) the crotch member transferring step S2, a part of the webs 61 and 62 (the webs 6A and 6B) and a part o the backsheet 3 forming the crotch portion member 30 is cut. In other words, a gap AR to form the leg-surrounding opening portions 60 is formed in the webs 61 and 62.

In the folding step S4 after (downstream of) the leg-surrounding portion forming step S3, the web is folded into two by overlapping the web 61 on one side thereof and the web 62 on the other side thereof with each other along a folding line which is defined in the crotch portion member 30A and in parallel with the machine direction MD.

In the joining step S5 after (downstream of) the folding step S4, the front waistline portion 10 and the back waistline portion 20 are joined in joint regions 40A prepared to form the joint portions 40 by ultrasonic treatment or heat treatment. The joint regions 40A are formed on both sides of an imaginary line SL indicating a to-be-cut position extending in a cross direction CD of an intermediate web 6.

In the cutting step S6 after (downstream of) the joining step S5, the intermediate web 6 joined in the joint regions 40A is cut in the machine direction MD at predetermined intervals, that is, along the imaginary line SL, whereby absorbent articles 1 are manufactured.

(Ultrasonic Joining Apparatus)

Figure 3:
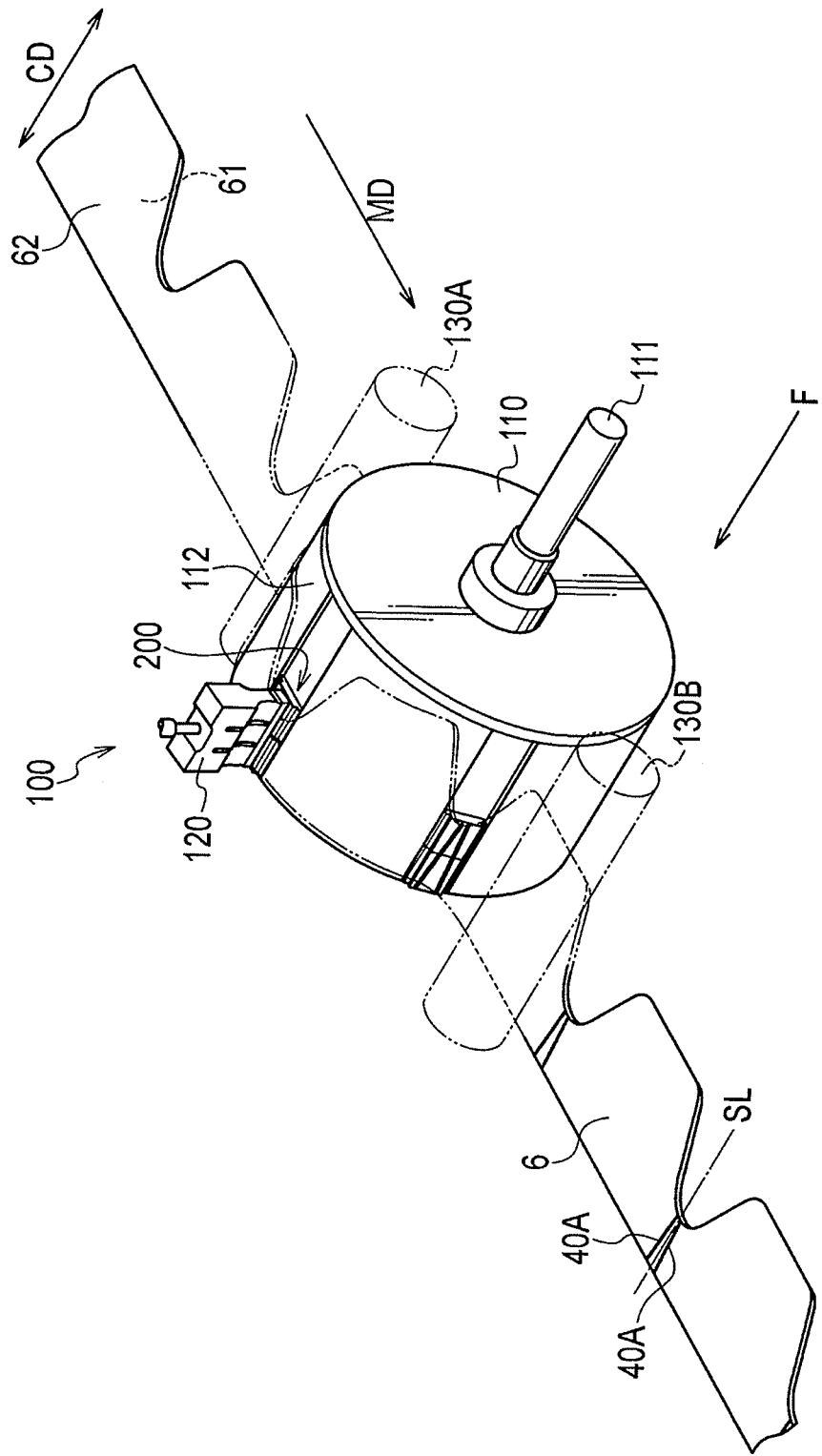
FIG. 3 is a perspective view showing a part of an ultrasonic joining apparatus according to this embodiment.
Figure 4:
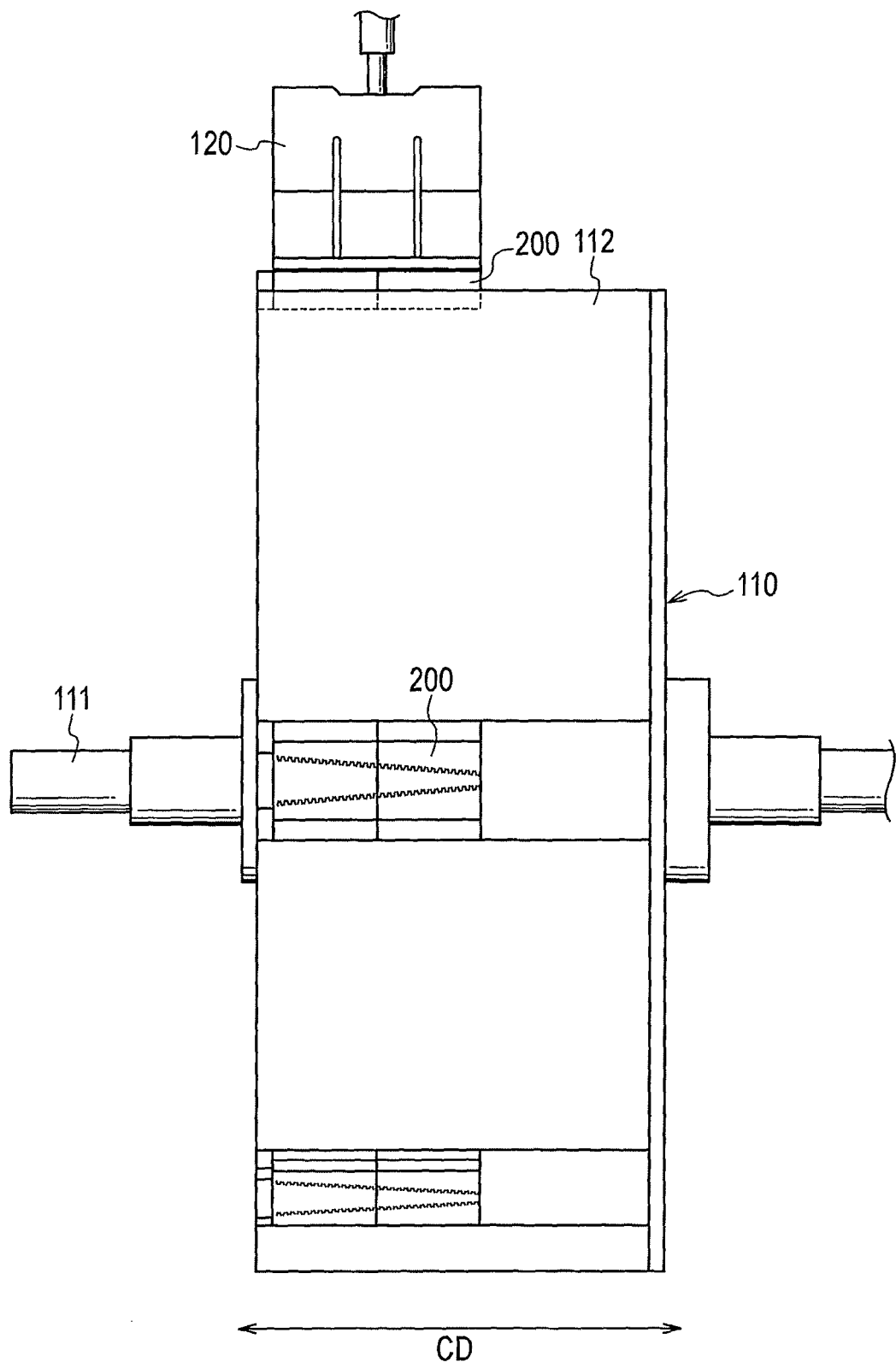
FIG. 4 is a side view showing the ultrasonic joining apparatus according to this embodiment seen from the downstream side.

An ultrasonic joining apparatus 100 is used to perform the joining step S5. A configuration of the ultrasonic joining apparatus 100 according to this embodiment is described below with reference to the drawings. FIG. 3 is a view illustrating the joining step S5 in a direction F. FIG. 4 is a side view showing the ultrasonic joining apparatus 100 seen in the machine direction MD from the downstream side. For the sake of explanation, no intermediate web 6 is illustrated in FIG. 4.

The ultrasonic joining apparatus 100 includes a rotating drum 110 and an ultrasonic horn 120 configured to output ultrasonic vibrations.

Anvils 200 are provided on an outer peripheral surface 112 of the rotating drum 110. A rotational shaft 111 of the rotating drum 110 extends in parallel with the cross direction CD orthogonal to the machine direction MD in which the manufacturing processes flow. The rotating drum 110 and the ultrasonic horn 120 are arranged to face each other with the intermediate web 6 interposed therebetween, the intermediate web 6 being obtained by overlapping the web 61 on one side and the web 62 on the other side with each other.

The ultrasonic horn 120 is coupled to an ultrasonic vibrator via a booster not shown. The ultrasonic horn 120 applies, on the intermediate web 6, ultrasonic vibrations generated by the ultrasonic vibrator and then amplified by the booster. The ultrasonic horn 120 comes into contact with each joint region 40A of the intermediate web 6, and is pressed against one of the anvils 200 described later with the intermediate web 6 interposed therebetween. The contact pressure of the ultrasonic horn 120 against the intermediate web 6 is adjustable.

The ultrasonic joining apparatus 100 is provided with a roll 130A on the upstream side in its flow direction, and a roll 130B on the downstream side in the flow direction. The intermediate web 6 is conveyed in the machine direction MD while being pressed against the outer peripheral surface 112 of the rotating drum 110 by the rolls 130A and 130B. The ultrasonic joining apparatus 100 causes the anvil 200 and the ultrasonic horn 120 to pinch each joint region 40A of the intermediate web 6 between them, and thereby performs ultrasonic joining on the joint region 40A.

(Structure 1 of Anvil)

Figure 5:
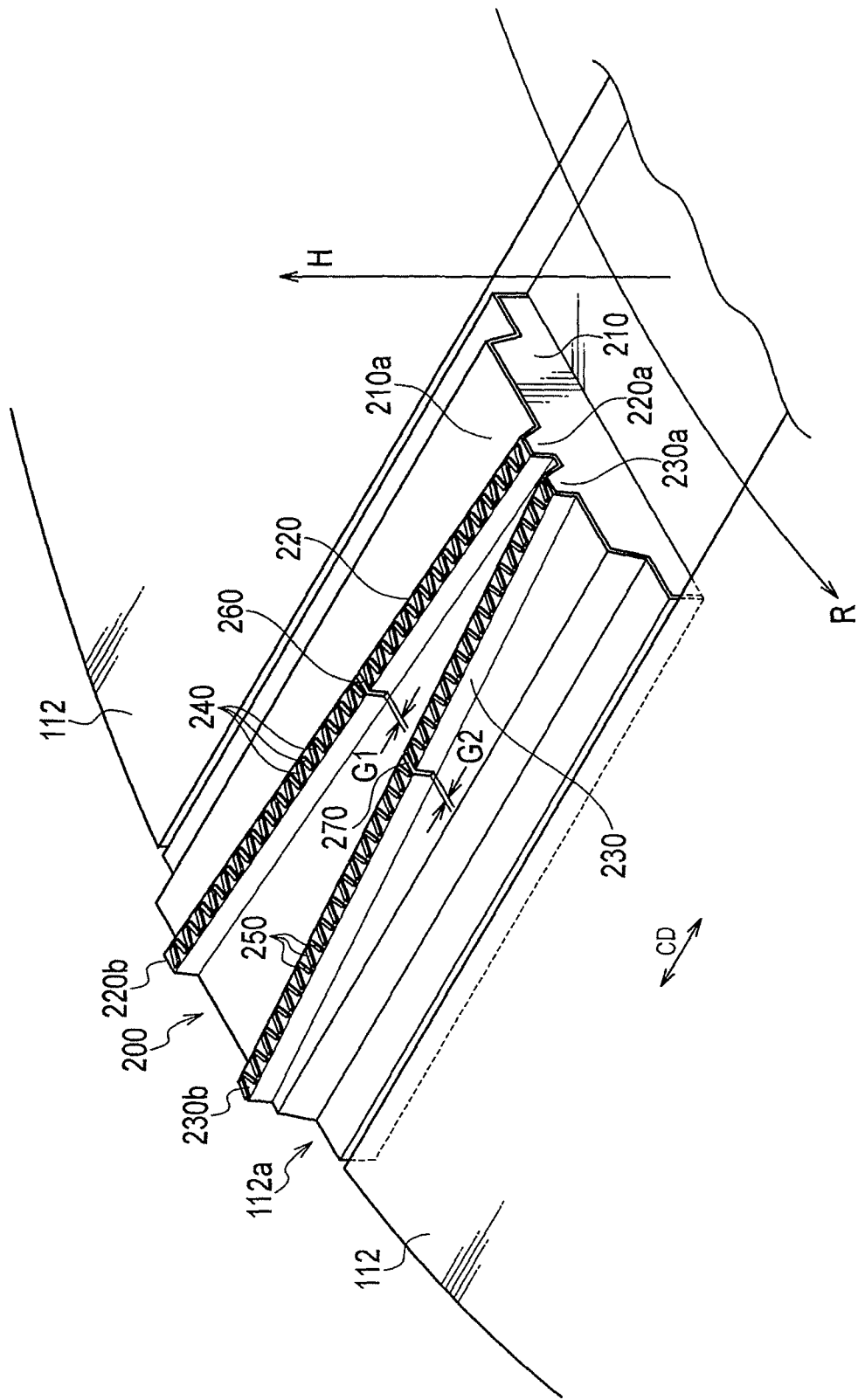
FIG. 5 is a perspective view for explaining an anvil according to this embodiment.

Next, a structure of each anvil 200 is described by using FIG. 5. The anvil 200 includes a base 210 and projections 220 and 230. The base 210 is installed at an attachment position 112a on the outer peripheral surface 112 of the rotating drum 110. The projection 220 protrudes from a front surface 210a of the base 210 in a normal direction H of the rotating drum 110. The projection 220 is formed in a line shape extending in the cross direction CD along the front surface 210a of the base 210.

The projection 220 includes multiple protrusions 240. Each protrusion 240 protrudes from the front surface of the projection 220 in the normal direction H. On the front surface 210a of the base 210, one end 220a in the cross direction CD of the projection 220 is provided forward of the other end 220b in a rotation direction R. In the projection 220, a cut portion 260 is formed to extend in a direction opposite to the protrusion direction of each protrusion 240. The cut portion 260 extends from the front surface of the projection 220 to the vicinity of the middle of the projection 220, the projection 220 protruding from the front surface 210a of the base 210.

In the embodiment shown in FIG. 5, the projection 230 is further formed on the base 210. The projection 230 includes multiple protrusions 250. Each protrusion 250 protrudes from the front surface of the projection 230 in the normal direction H. On the front surface 210a of the base 210, one end 230b in the cross direction CD of the projection 230 is provided forward of the other end 230a in the rotation direction R. In the projection 230, a cut portion 270 is formed to extend in a direction opposite to the protrusion direction of each protrusion 250. The cut portion 270 extends from the front surface of the projection 230 to the vicinity of the middle of the projection 230, the projection 230 protruding from the front surface 210a of the base 210.

When the ultrasonic horn 120 is pressed against the intermediate web 6, the intermediate web 6 is heated from the inside thereof and melted, and pressed against the protrusions 240 and 250 protruding from the projections 220 and 230. As a result, a convexo-concave joint pattern is formed on the intermediate web 6.

Gaps G1 and G2 of the cut portions 260 and 270, which are measured along the projections 220 and 230 respectively, each have a length of 1 mm, for example. The gap G1 is preferably narrower than the interval between the adjacent two protrusions 240, and the gap G2 is preferably narrower than the interval between the adjacent two protrusions 250.

Further, since the length of the joint portion 40 is 130 mm in the case of a diaper for adults, the length of each of the projections 220 and 230 in the cross direction CD is preferably 130 mm or larger.

In the anvil 200 shown in FIG. 5, the interval between the end 220a of the projection 220 and the end 230a of the projection 230 in the rotation direction R is narrower than the end 220b of the projection 220 and the end 230b of the projection 230 in the rotation direction R. In this manner, the ends 220a and 230b of the projections 220 and 230 are each provided forward of its counterpart in the rotation direction R. This allows reducing impact and resistance that the anvil 200 receives from the ultrasonic horn 120 when being pressed against the ultrasonic horn 120 with the intermediate web 6 interposed therebetween.

The anvil 200 described by using FIG. 5 includes the cut portion 260 extending from the front surface of the projection 220 to the vicinity of the middle of the projection 220, and the cut portion 270 extending from the front surface of the projection 230 to the vicinity of the middle of the projection 230.

This allows reducing the mutual interference of vibrations, which are generated by the ultrasonic horn 120, in the anvil 200 even with the anvil 200 bigger in size than that used in manufacturing a diaper for children. This thereby allows reducing the accumulation of damages, which are caused by the mutual interference of ultrasonic vibrations in the anvil 200, in a spot of the anvil 200 or in a peripheral member connected to the anvil 200. As a result, it is possible to prevent shortening the time to replace the anvil 200 or the peripheral member, and thus to suppress an increase in manufacturing costs. Further, damages caused by ultrasonic vibrations and accumulated in the anvil 200 can be reduced. This allows reducing a decrease in ultrasonic joining quality due to the damages of the anvil 200, and thus allows a stable ultrasonic joining process.

In the anvil 200 shown in FIG. 5, the base 210 may be detachable at the attachment position 112a. Such a separately detachable anvil 200 eliminates the need for replacing the entire rotating drum when a part of the anvils 200 are damaged, thereby reducing costs for replacement.

Each of the projections 220 and 230 is formed across the width in the cross direction CD of the base 210. However, the position of each of the ends 220a and 230a does not necessarily have to be equal to that in the cross direction CD of the corresponding end of the base 210, and the position of each of the ends 220b and 230b does not necessarily have to be equal to that in the cross direction CD of the other end of the base 210.

(Structure 2 of Anvil) Next, a different embodiment of the anvil is described. Hereinafter, a component having the same effect as that in the above embodiment is given the same number and detailed description thereof is omitted.

Figure 6:
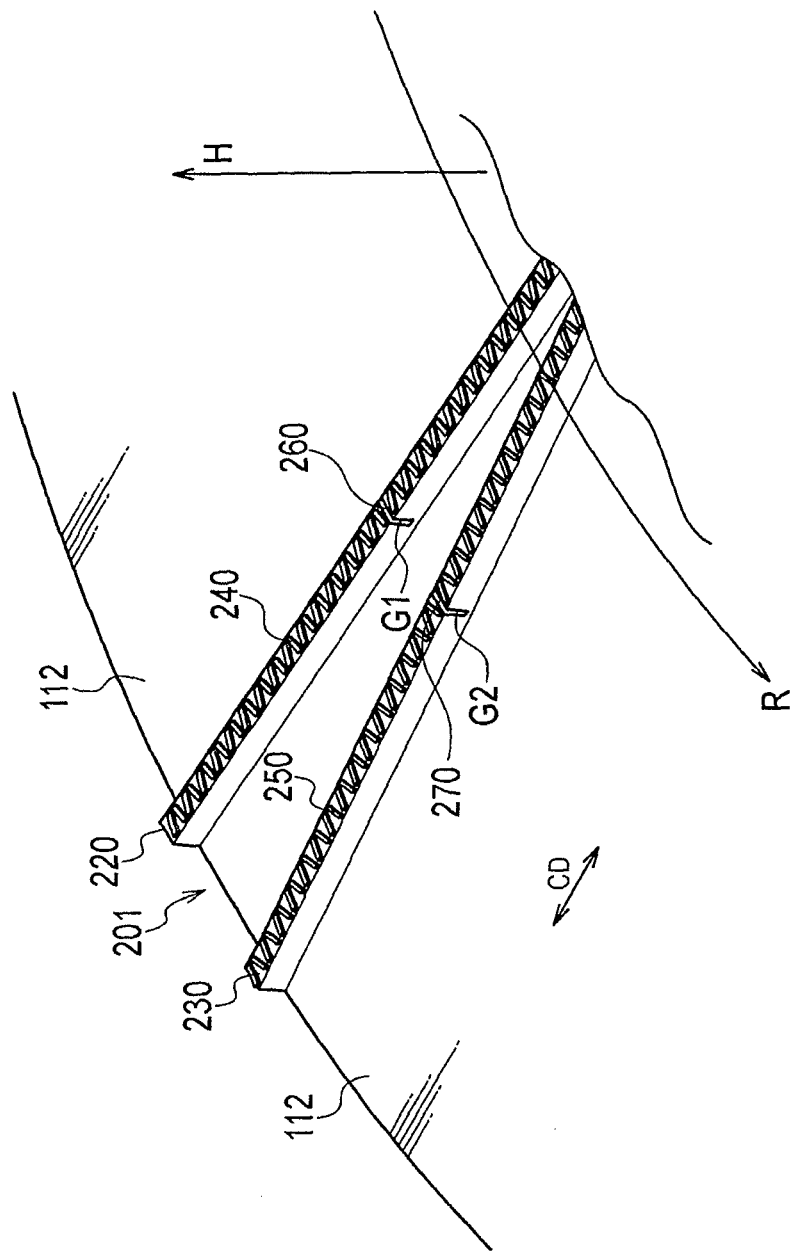
FIG. 6 is a perspective view for explaining a modification of the anvil according to this embodiment.

FIG. 6 shows the different embodiment of the anvil. The anvil does not necessarily have to include the base 210. To be more specific, an anvil 201 has the projections 220 and 230 arranged on the outer peripheral surface 112 of the rotating drum 110. The projections 220 and 230 have the respective cut portions 260 and 270 formed therein. The cut portions 260 and 270 may extend to the vicinity of the middle of the projections 220 and 230, or may divide the projections 220 and 230. Even if the projections 220 and 230 are arranged directly on the outer peripheral surface 112 of the rotating drum 110 in the above manner, the cut portions 260 and 270 provided in the projections 220 and 230 allow obtaining an effect of reducing the mutual interference of vibrations, which are generated by the ultrasonic horn 120, in the anvil 201.

(Structure 3 of Anvil)

Figure 7:
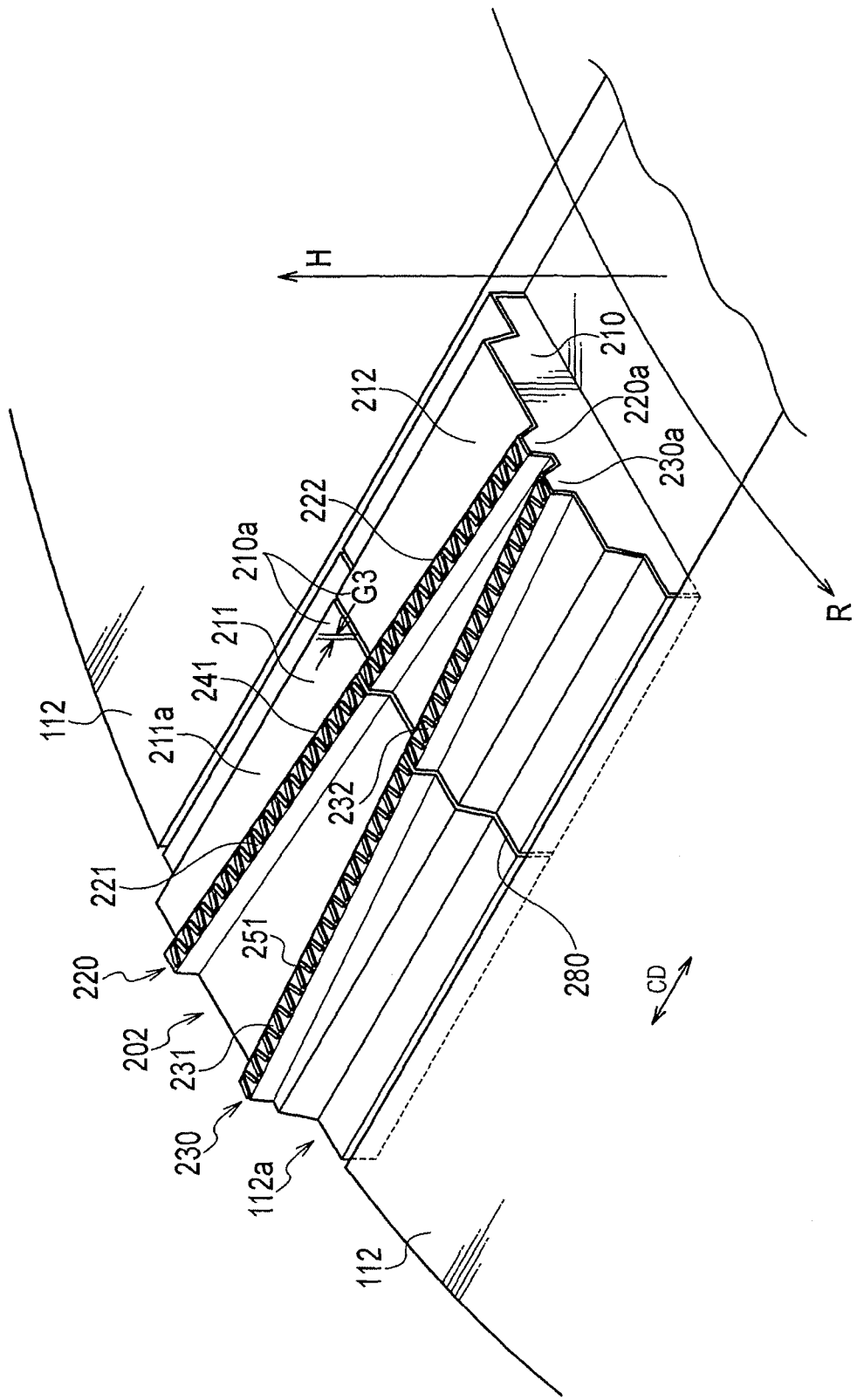
FIG. 7 is a perspective view for explaining a different embodiment of the anvil according to this embodiment.

An anvil 202 shown in FIG. 7 is divided into a base 211 and a base 212 by a cut portion 280 formed in the front surface 210a of the base 210. Moreover, the projection 220 is divided into a projection 221 and a projection 222, and the projection 230 is divided into a projection 231 and a projection 232.

The projections 221 and 231 are formed on the base 211. The projections 221 and 231 protrude from a front surface 211a of the base 211 in the normal direction H of the rotating drum 110. Each of the projections 221 and 231 is formed in a line shape extending in the cross direction CD along the front surface 211a of the base 211. The projection 221 includes multiple protrusions 241, and the projection 231 includes multiple protrusions 251. Each protrusion 241 protrudes from the front surface of the projection 221 in the normal direction H, and each protrusion 251 protrudes from the front surface of the projection 231 in the normal direction H.

The projections 222 and 232 are formed on the base 212 as similar to those on the base 211. The projections 221 and 222 are formed along a single line. Accordingly, a set of the projections 222 and 221, and a set of the projections 232 and 231 each form one joint region 40A on the intermediate web 6. In the case of a diaper for adults, the length of each joint portion 40 is 130 mm. A gap G3 of the cut portion 280 has a length of 1 mm, for example. The gap G3 is preferably narrower than the interval between the adjacent two protrusions 241 or the interval between the adjacent two protrusions 251.

The base 210 of the anvil 202 described by using FIG. 7 is divided by the cut portion 280. Accordingly, the effect of reducing the mutual interference of vibrations, which are generated by the ultrasonic horn 120, in the anvil 202 is enhanced. This allows reliably reducing the accumulation of damages, which are caused by the mutual interference of ultrasonic vibrations in the anvil 202, in a spot of the anvil 202 or in a peripheral member connected to the anvil 202. As a result, it is possible to prevent shortening the time to replace the anvil or the peripheral member, and thus to suppress an increase in manufacturing costs.

(Structure 4 of Anvil)

Figure 8:
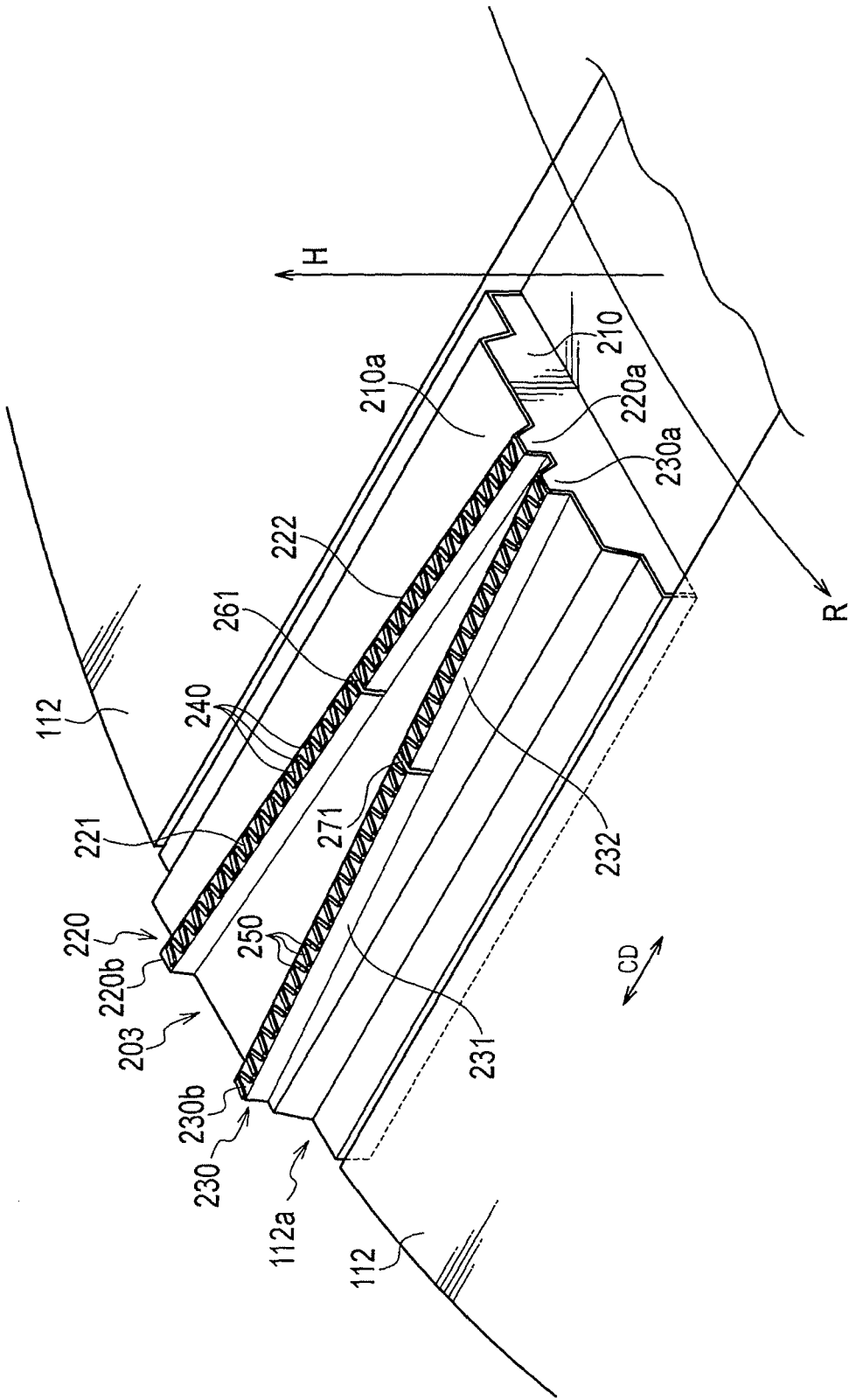
FIG. 8 is a perspective view for explaining a different embodiment of the anvil according to this embodiment.

In an anvil 203 shown in FIG. 8, the base 210 is a single body, but the projections 220 and 230 are divided by cut portions 261 and 271, respectively. In this case also, the effect of reducing the mutual interference of vibrations, which are generated by the ultrasonic horn 120, in the anvil 203 can be obtained. As a result, it is possible to prevent shortening the time to replace the anvil or its peripheral member, and thus to suppress an increase in manufacturing costs.

(Structure 5 of Anvil)

Figure 9:
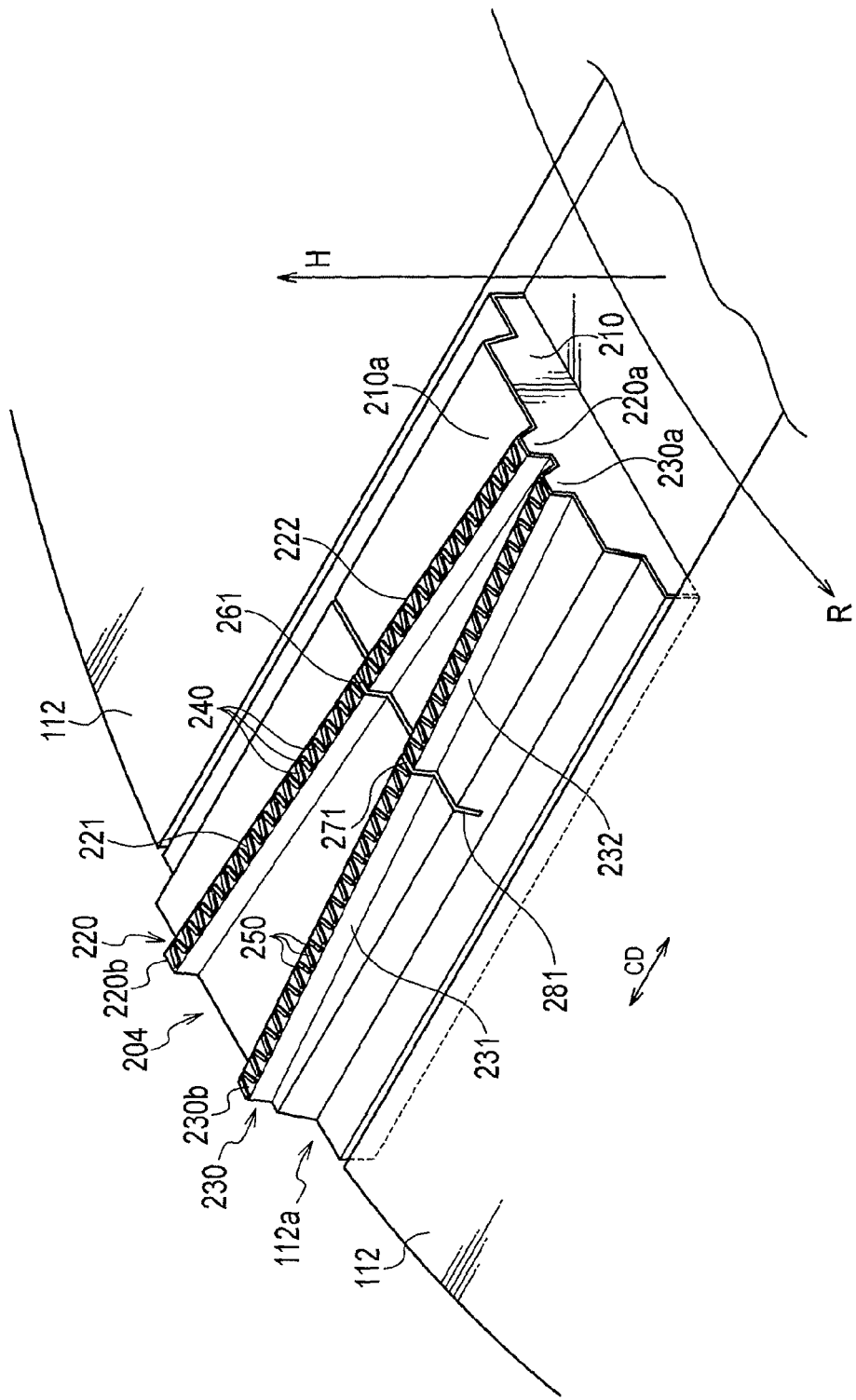
FIG. 9 is a perspective view for explaining a different embodiment of the anvil according to this embodiment.

In an anvil 204 shown in FIG. 9, the projections 220 and 230 are divided by the cut portions 261 and 271, respectively. A cut portion 281 is formed in the base 210 to extend continuously from the cut portions 261 and 271 dividing the projections 220 and 230 and extend in a direction opposite to the normal direction H. Since the cut portions 261 and 271 divide the projections 220 and 230 and the cut portion 281 is formed in the base 210, the effect of reducing the mutual interference of vibrations, which are generated by the ultrasonic horn 120, in the anvil 204 can be enhanced. As a result, it is possible to prevent shortening the time to replace the anvil or its peripheral member, and thus to suppress an increase in manufacturing costs.

(Structure 6 of Anvil)

Figure 10:
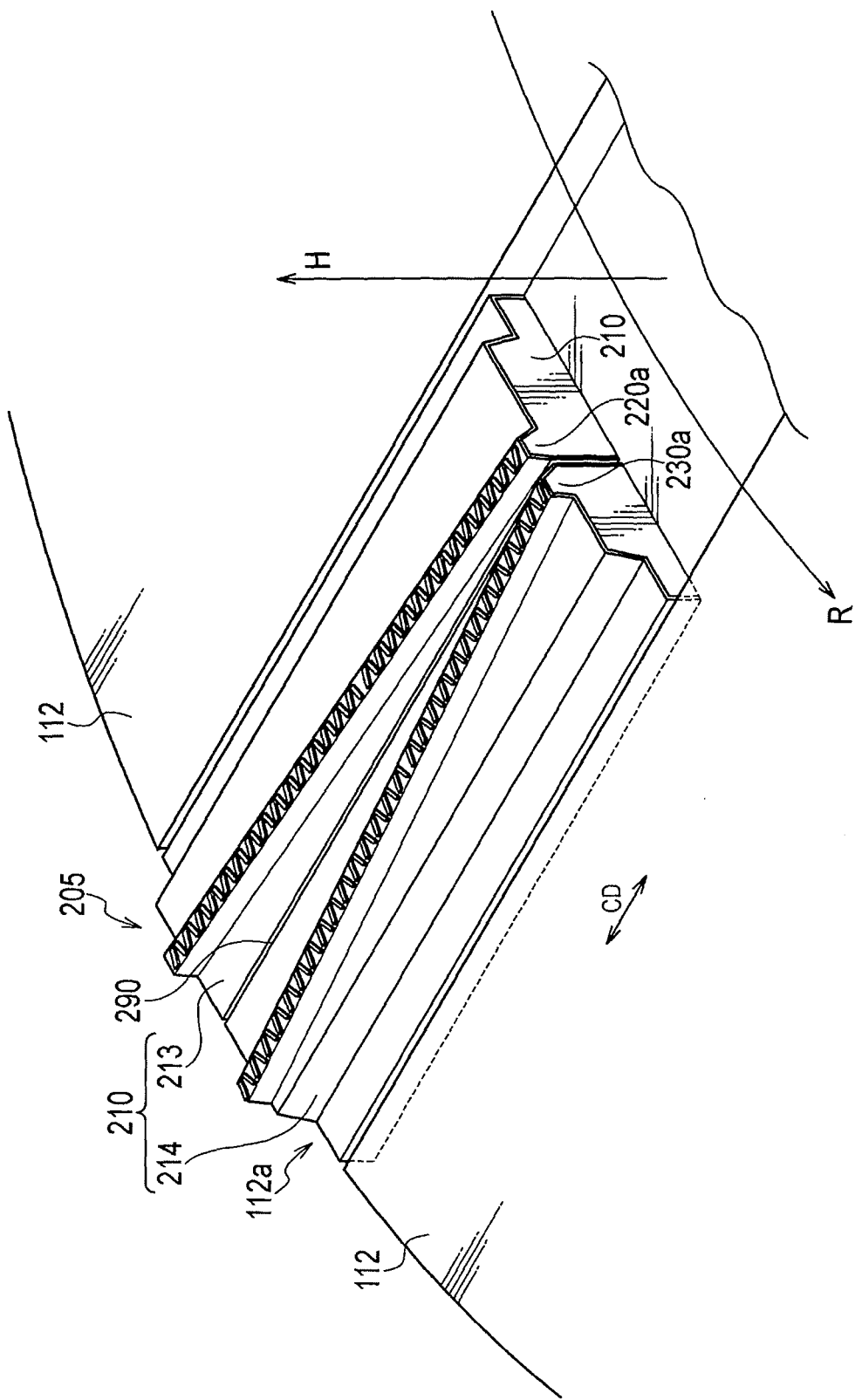
FIG. 10 is a perspective view for explaining a different embodiment of the anvil according to this embodiment.

In an anvil 205 shown in FIG. 10, the base 210 is divided by a cut portion 290 extending in a direction orthogonal to the rotation direction R of the rotating drum 110. In other words, the anvil 205 is divided into a base 213 arranged on a side which comes earlier in the rotation in the rotation direction R, and a base 214 arranged on a side which comes later. The anvil 205 shown in FIG. 10 allows reducing the mutual interference of vibrations, which are generated by the ultrasonic horn 120, in the anvil 205. As a result, it is possible to prevent shortening the time to replace the anvil or its peripheral member, and thus to suppress an increase in manufacturing costs.

(Structure 7 of Anvil)

The anvil 200 shown in FIG. 5 does not necessarily have to include the projections 220 and 230. In an anvil 206 shown in FIG. 11, the multiple protrusions 240 and 250 are formed on the front surface 210a of the base 210. A cut portion 291 is formed in the base 210 to extend in a direction opposite to the protrusion direction of each protrusion.

(Structure 8 of Anvil)

Figure 12:
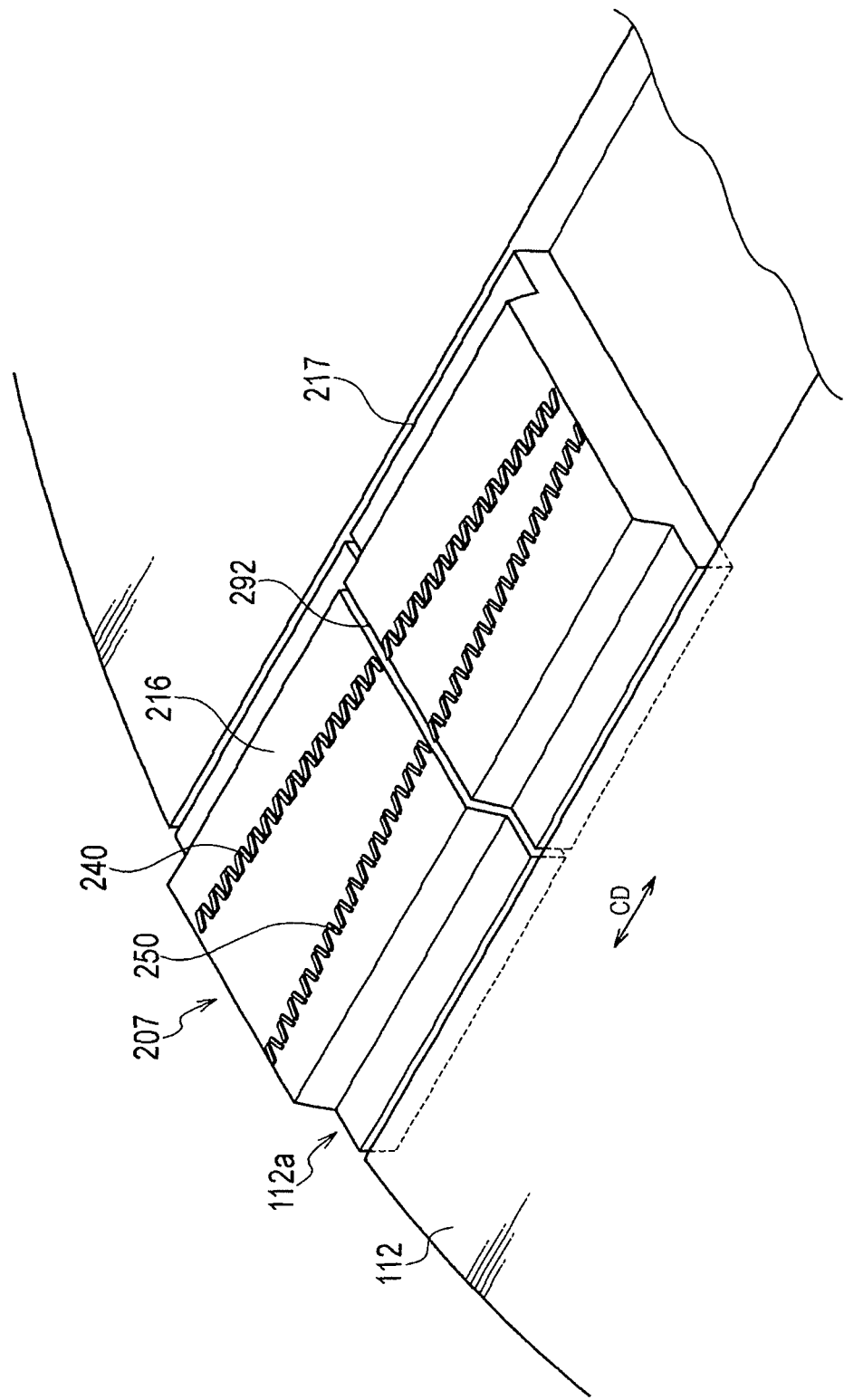
FIG. 12 is a perspective view for explaining a different embodiment of the anvil according to this embodiment.

In an anvil 207 shown in FIG. 12, the base 210 is divided by a cut portion 292. In other words, the anvil 207 includes a base 216 and a base 217.

Figure 11:
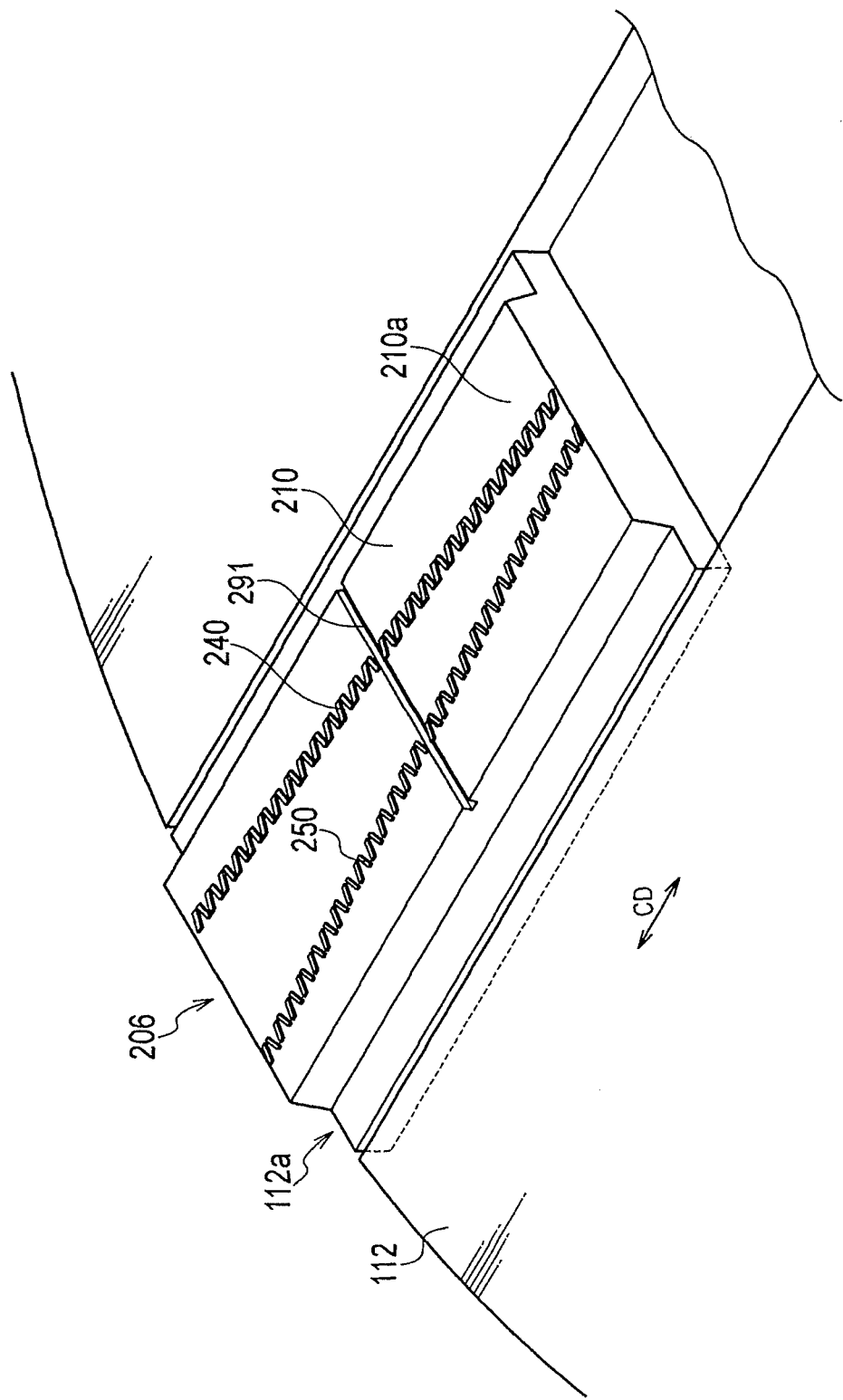
FIG. 11 is a perspective view for explaining a different embodiment of the anvil according to this embodiment.

The provision of the cut portions 291 and 292 allows reducing the mutual interference of vibrations, which are generated by the ultrasonic horn 120, in the anvils 206 and 207 even if the multiple protrusions are arranged directly on the base as shown in FIGS. 11 and 12. As a result, it is possible to prevent shortening the time to replace the anvil or its peripheral member, and thus to suppress an increase in manufacturing costs.

(Modification of Ultrasonic Horn)

In the above embodiment, the description has been given of the ultrasonic horn 120 generating ultrasonic vibrations with one ultrasonic vibrator. However, the ultrasonic horn 120 may be provided in plurality.

In general, there are constraints between the performance of an ultrasonic vibrator and the size of an ultrasonic horn due to the principle of ultrasonic vibrations. With energy loss taken into consideration, the size of an ultrasonic horn which leads to the most efficient operation is limited. In the steps of manufacturing a diaper for adults, the joint region in which to perform ultrasonic joining is larger in size than in the steps of manufacturing a diaper for children. Thus, multiple ultrasonic horns are arranged in parallel with each other in the cross direction CD.

In an example shown in FIG. 13, an ultrasonic horn 121a and an ultrasonic horn 121b are arranged in parallel with each other in the cross direction CD and thus formed into a single unit. The multiple ultrasonic horns are likely to generate interference waves between adjacent ultrasonic horns. In this case, it is preferable to form a cut portion in a position to divide the anvil into a region to be pressed against the ultrasonic horn 121a with the intermediate web 6 interposed therebetween, and a region to be pressed against the ultrasonic horn 121b with the intermediate web 6 interposed therebetween.

For example, any of the cut portions 260 and 270 shown in FIGS. 5 and 6, the cut portion 280 shown in FIG. 7, the cut portions 261 and 271 shown in FIG. 8, the cut portions 261 and 271 shown in FIG. 9, and the cut portions 291 and 292 shown in FIG. 11 is formed in the position to divide the anvil into the region to be pressed against the ultrasonic horn 121a with the intermediate web 6 interposed therebetween, and the region to be pressed against the ultrasonic horn 121b with the intermediate web 6 interposed therebetween. This allows reliably reducing the interference between vibrations generated by each ultrasonic horn.

Other Embodiments

As described above, the details of the present invention have been disclosed through the embodiment of the present invention. It should not be understood that the description and drawings which constitute part of this disclosure limit the present invention. Based on this disclosure, those skilled in the art may easily come up with various alternative embodiments, examples and operation techniques.

For example, in the above embodiment of the present invention, the description has been given of the case where a joint pattern is formed in the joint regions of the waist lateral-side portions. However, the present invention is not limited to this case. Ultrasonic joining may be applied on any required part.

Further, the description has been provided for the absorbent article 1 formed in combination of the front waistline portion 10, the back waistline portion 20, and the crotch portion 30 (so-called three-piece type). However, the absorbent article 1 is not limited to this structure. Alternatively, the absorbent article 1 may be formed by integrating the front waistline portion 10, the back waistline portion 20, and the crotch portion 30 as a single unit (so-called one-piece type).

Additionally, the description has been provided for the absorbent article 1 as a pants-type disposal diaper. However, the absorbent article 1 is not limited to this. The present invention is applicable to other articles for which the joining step S5 is used (such as an open-type diaper and a napkin). Moreover, needless to say, the structure of the absorbent article 1 is not limited to that described in the above embodiment, but may be set appropriately in accordance with any intended use.

As described above, the present invention naturally includes various embodiments which are not described herein. Accordingly, the technical scope of the present invention should be determined only by the matters to define the invention in the scope of claims regarded as appropriate based on the description. Note that, the entire content of Japanese Patent Application No. 2009-180199 (filed on Jul. 31, 2009) is incorporated herein by reference.

[Industrial Applicability]

The present invention can provide an ultrasonic joining apparatus capable of enhancing ultrasonic joining quality and performing a stable ultrasonic joining process. The present invention can also provide an absorbent article manufacturing apparatus capable of enhancing ultrasonic joining quality and stably producing a pants-type absorbent article in manufacturing the absorbent article.

The invention claimed is:

1. An ultrasonic joining apparatus comprising:
a rotating drum having an anvil formed on an outer peripheral surface of the rotating drum; and
an ultrasonic horn configured to output ultrasonic vibrations, wherein
the rotating drum has a rotational shaft extending in parallel with a cross direction orthogonal to a machine direction in which manufacturing processes flow,
the rotating drum and the ultrasonic horn are arranged to face each other with an intermediate web interposed therebetween, the intermediate web including a first web and a second web overlapping with each other,
the anvil and the ultrasonic horn pinch a certain region of the intermediate web, which is conveyed in the machine direction, to perform ultrasonic joining on the certain region,
the anvil includes:
a projection protruding in a normal direction of the rotating drum and being formed in a line shape extending in the cross direction; and
a plurality of protrusions protruding from the projection in the normal direction, and
the projection has a cut formed therein, the cut extending in a direction opposite to a protrusion direction of the protrusions.

2. The ultrasonic joining apparatus according to claim 1, wherein the ultrasonic horn is provided in plurality, and the cut divides the projection into regions which respectively correspond to the plurality of ultrasonic horns.

3. The ultrasonic joining apparatus according to claim 1, wherein
the anvil is detachably attached to the outer peripheral surface of the rotating drum, and includes a base which protrudes from the outer peripheral surface of the rotating drum in the normal direction of the rotating drum and in a line shape extending in the cross direction, and the projection is formed on a front surface of the base.

4. The ultrasonic joining apparatus according to claim 3, wherein the projection is divided by the cut.

5. The ultrasonic joining apparatus according to claim 3, wherein a cut is formed in the base, and coupled to the cut dividing the projection.

6. The ultrasonic joining apparatus according to claim 1, wherein the anvil includes a base which protrudes from the outer peripheral surface of the rotating drum in the normal direction of the rotating drum and is formed in a line shape extending in the cross direction,
the projection is formed on a front surface of the base, and
one end in the cross direction of the projection is provided forward of the other end thereof in a rotation direction.

7. An absorbent article manufacturing apparatus comprising:
a rotating drum having an anvil formed on an outer peripheral surface of the rotating drum; and
an ultrasonic horn configured to output ultrasonic vibrations, wherein
the rotating drum has a rotational shaft extending in parallel with a cross direction orthogonal to a machine direction in which manufacturing processes flow,
the rotating drum and the ultrasonic horn are arranged to face each other with an intermediate web interposed therebetween, the intermediate web including a first web to form a front waistline portion of an absorbent article and a second web to form a back waistline portion of the absorbent article overlapping with each other,
the absorbent article includes: the front waistline portion to be fitted to a front waist of a wearer; the back waistline portion to be fitted to a back waist of the wearer; a crotch portion to be fitted to a crotch of the wearer; and leg-surrounding opening portions which open at both sides of the crotch portion,
the anvil and the ultrasonic horn pinch a certain region of the intermediate web, which is conveyed in the machine direction, to perform ultrasonic joining on the certain region,
the anvil includes:
a projection protruding in a normal direction of the rotating drum and being formed in a line shape extending in the cross direction; and
a plurality of protrusions protruding from the projection in the normal direction, and
the projection has a cut formed therein, the cut extending in a direction opposite to a protrusion direction of the protrusions.

* * * * *